(12) United States Patent
Kawagishi et al.

(10) Patent No.: US 6,663,565 B2
(45) Date of Patent: Dec. 16, 2003

(54) ULTRASOUND DIAGNOSTIC APPARATUS

(75) Inventors: Tetsuya Kawagishi, Kuroiso (JP);
Takeshi Sato, Nasu-gun (JP);
Yoshitaka Mine, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/186,703

(22) Filed: Jul. 2, 2002

(65) Prior Publication Data

US 2003/0018259 A1 Jan. 23, 2003

(30) Foreign Application Priority Data

Jul. 3, 2001 (JP) ....................................... 2001-202549

(51) Int. Cl.⁷ ................................................ A61B 8/00
(52) U.S. Cl. ........................................ 600/437; 600/443
(58) Field of Search ................................. 600/500, 501, 600/502, 443, 444, 447, 448, 449

(56) References Cited

U.S. PATENT DOCUMENTS

| | | | |
|---|---|---|---|
| 5,014,712 A | 5/1991 | O'Donnell | |
| 5,938,611 A | 8/1999 | Muzilla et al. | |
| 5,961,463 A | 10/1999 | Rhyne et al. | |
| 6,146,328 A | 11/2000 | Chiao et al. | |
| 6,277,075 B1 * | 8/2001 | Torp et al. | 600/443 |
| 6,312,384 B1 | 11/2001 | Chiao | |
| 6,334,850 B1 * | 1/2002 | Amano et al. | 600/500 |

\* cited by examiner

*Primary Examiner*—Francis J. Jaworski
*Assistant Examiner*—Maulin M. Patel
(74) *Attorney, Agent, or Firm*—Oblon, Spivak, McClelland, Maier & Neustadt, P.C.

(57) ABSTRACT

A transmitting/receiving unit transmits an ultrasound wave to an object at a first rate in accordance with a first code, transmit an ultrasound wave to the object at a second rate in accordance with a second code complementary to the first code, and receives the first and second reception signals. The first and second reception signals are convoluted in the second and first codes respectively. The phase difference between the two signals represents the motion of the tissue of the object between the first and second rates. The first or second reception signal is compensated on the basis of the phase difference. The compensated first and second reception signals are convoluted in the first and second codes respectively. The two signals are added to generate a third reception signal. Image data is generated on the basis of the third reception signal.

20 Claims, 6 Drawing Sheets

ULTRASOUND DIAGNOSTIC APPARATUS

CROSS-REFERENCE TO RELATED APPLICATIONS

This application is based upon and claims the benefit of priority from the prior Japanese Patent Application No. 2001-202549, filed Jul. 3, 2001, the entire contents of which are incorporated herein by reference.

BACKGROUND OF THE INVENTION

1. Field of the Invention

The present invention relates to an ultrasound diagnostic apparatus for transmitting/receiving ultrasound waves by using a pulse compression technique.

2. Description of the Related Art

A pulse compression technique is a technique developed in the field of radars. An increase in maximum radar range requires an increase in transmission pulse length. An increase in maximum radar range, however, degrades distance resolution. Pulse compression has been developed to attain an increase in maximum radar range and an improvement in distance resolution. Pulse compression is performed by using a transmission pulse having a long pulse length obtained by performing special modulation inside a pulse. The pulse length is substantially decreased by demodulating the reception signal.

Pulse compression schemes are classified into a linear frequency modulation pulse compression scheme and a phase-coded pulse compression scheme. In the linear frequency modulation pulse compression scheme, a chirp signal that is frequency-modulated such that the frequency linearly changes is transmitted. The reception signal is demodulated by a circuit having a frequency/delay time characteristic reverse to transmission frequency modulation. With this operation, dispersed frequency components are concentrated to one point.

In the phase-coded pulse compression scheme, the phase of a reference waveform signal is discretely modulated $(0, \pi)$ in accordance with a code series (a series of 1 and −1). The phase of the reception signal is modulated with a code series reverse to the transmission code series.

As is known, the waveform after pulse compression does not theoretically have a single component, and small components called range sidelobes appear on both sides of a central component. As a means for reducing such range sidelobes, a pair of code series called a Golay codes has been found.

The Golay codes are constituted by a pair of complementary code series (FIGS. 1A and 1B). A reference signal 100 phase-modulated in accordance with one code (FIG. 1A) is transmitted, and a reception signal 101 (FIG. 1C) is acquired. Likewise, at the next rate, a signal 200 phase-modulated in accordance with the other code (FIG. 1B) is transmitted, and a reception signal 201 (FIG. 1D) is acquired. The reception signal 101 is convoluted with the corresponding signal 100 to generate a demodulated signal 102 (FIG. 1E). Likewise, the reception signal 201 is convoluted with the corresponding phase-modulation signal 200 to generate a demodulated signal 202 (FIG. 1F). The reception signals 102 and 202 are added (FIG. 1G). With this operation, a signal 300 in which range sidelobes cancel out each other can be obtained.

Studies have been made to apply the above pulse compression technique, especially the phase-coded pulse compression technique using a Golay code, to ultrasound diagnosis.

This application is, however, hindered by causes unique to ultrasound diagnosis. The greatest cause is the motion of the tissue (reflecting/scattering body). The motion of the tissue between two rates causes a phase difference corresponding to the motion between signals with the two rates. As a consequence, range sidelobes remain.

In order to solve this problem, a phase change due to the motion of the tissue between the rates must be obtained, and phase compensation must be performed with respect to a pair of reception signals. As a typical method for such operation, a method using a Doppler technique is available, in which transmission/reception is repeated at least at two rates, the complex number of a signal with one rate at each depth is multiplied by the complex number of a signal with the other rate at the corresponding depth, and a phase argument is obtained from the multiplication result. In the autocorrelation method, similar processing is performed between a plurality of rates to obtain a complex vector product. This case can be regarded as a special case to which the autocorrelation method is applied, in which the number of data is two. When the obtained phase argument is normalized with $2\pi$, and the product of the normalized value and the wavelength of a barycentric frequency representing the fundamental wave is calculated, the displacement of the tissue between the two rates can be obtained.

This phase compensation (motion compensation) technique cannot be applied to the phase-coded pulse compression scheme using a Golay code. Since different transmission waveforms are used, reception signals differ in their waveforms between the rates even if the scattering body remains the same. This makes it impossible to extract only a phase difference due to the motion of the scattering body at each portion between signals.

BRIEF SUMMARY OF THE INVENTION

It is an object of the present invention to realize the use of a phase-coded pulse compression scheme for ultrasound diagnosis.

According to the first aspect of the present invention, there is provided an ultrasonic diagnostic apparatus comprising a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object, a first processor configured to convolute the second code in the first reception signal, convolute the first code in the second reception signal, and detect a phase difference between the two signals, the phase difference representing a motion of a tissue of the object between the first and second rates, a second processor configured to compensate at least one of the first and second reception signals on the basis of the phase difference, a third processor configured to convolute the first and second codes in the compensated first and second reception signals, respectively, add the two signals, and generate a third reception signal, and a unit configured to generate image data on the basis of the third reception signal.

According to the second aspect of the present invention, there is provided an ultrasonic diagnostic apparatus comprising a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object, a first processor configured to convolute the second code in the first reception signal, convolute the first code in the second reception signal, and detect a phase difference between the two signals, the phase difference representing a motion of a tissue of the object between the first and second rates, a second processor configured to convolute the first and second code in the compensated first and second reception signals, respectively, add the two signals upon giving a time shift corresponding to the phase difference, and generate a third reception signal, and a unit configured to generate image data on the basis of the third reception signal.

According to the third aspect of the present invention, there is provided an ultrasonic diagnostic apparatus comprising a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object, a first processor configured to convolute the second code in the first reception signal, convolute the first code in the second reception signal, and detect a cross-correlation function between the two signals, the cross-correlation function representing a motion of a tissue of the object between the first and second rates, a second processor configured to compensate at least one of the first and second reception signals on the basis of the cross-correlation function, a third processor configured to convolute the first and second code in the compensated first and second reception signals, respectively, add the two signals, and generate a third reception signal, and a unit configured to generate image data on the basis of the third reception signal.

According to the fourth aspect of the present invention, there is provided an ultrasonic diagnostic apparatus comprising a transmitting/receiving unit which transmits an ultrasound wave to an object to be examined in accordance with a first code signal with a first rate, receives a first reception signal, transmits an ultrasound wave to the object in accordance with a second code signal with a second rate, and receives a second reception signal from the object, a first processor which estimates a motion of a tissue in the object between the first and second rates on the basis of the first and second reception signals and the first and second code signals, a second processor which compensates the first and second reception signals on the basis of the estimated motion, and a unit which generates image data on the basis of the compensated first and second reception signals.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An imaging technique using a Golay code according to a preferred embodiment of the present invention will be described below with reference to the views of the accompanying drawing.

Figure 1G:
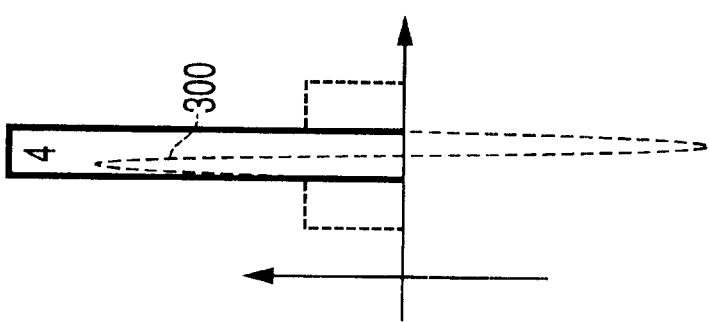
FIGS. 1A to 1G are charts for explaining a phase-coded pulse compression scheme using a Golay code in the prior art.
Figure 1C:
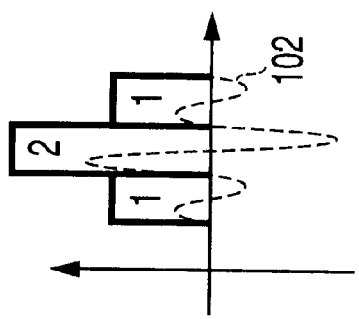
Figure 1D:
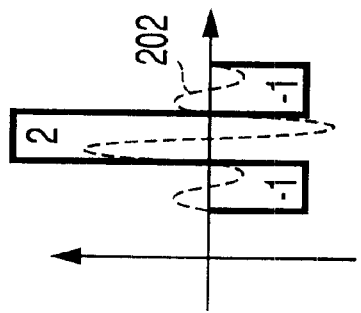
Figure 1E:
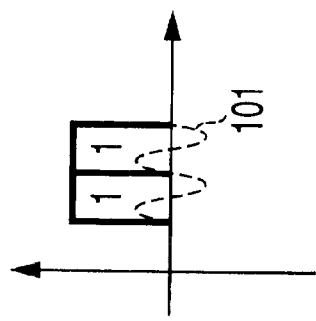
Figure 1F:
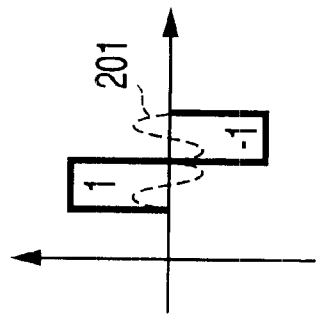
Figure 1A:
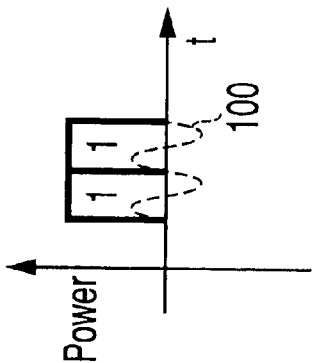
Figure 1B:
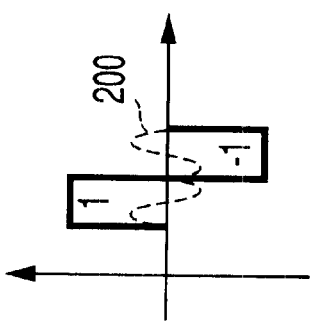
Figure 2:
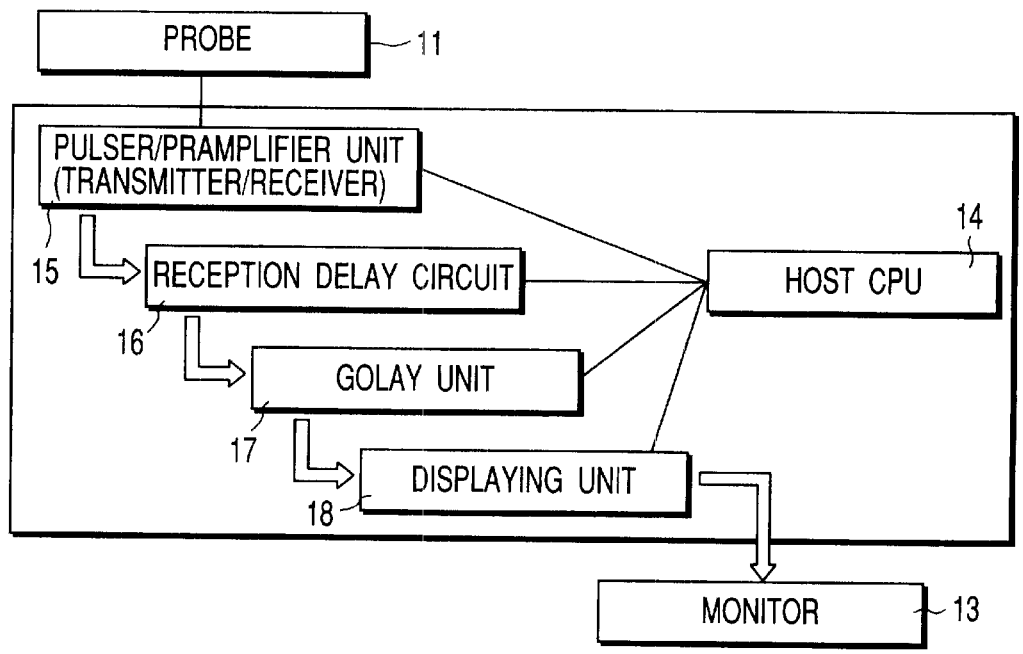
FIG. 2 is a block diagram showing the arrangement of an ultrasonic diagnostic apparatus according to an embodiment of the present invention.
Figure 3:
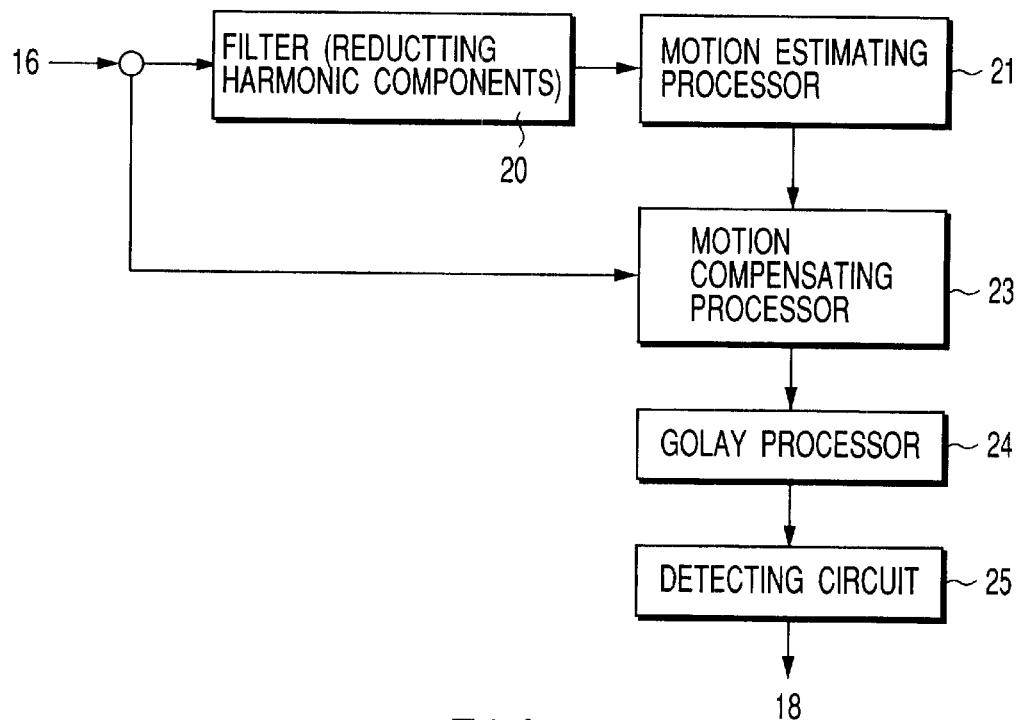
FIG. 3 is a block diagram showing the arrangement of a Golay processor in FIG. 2.

FIG. 2 shows the arrangement of an ultrasound diagnostic apparatus. FIG. 3 shows the arrangement of a Golay unit 17 in FIG. 2.

An ultrasound probe 11 has a plurality of transducer elements arranged one- or two-dimensionally. Transmission signals are supplied from a plurality of pulsers incorporated in a pulser/preamplifier unit 15 to the respective transducer elements. Each pulser modulates the phase of a reference waveform signal in accordance with a code series of "1" and "−1" supplied from a host CPU 14, and drives the corresponding transducer element in accordance with the phase-modulated signal (phase-modulated reference waveform signal).

The ultrasound waves transmitted from the plurality of transducer elements to an object to be examined are scattered at an acoustic impedance boundary in the tissue. Some of the scattered ultrasound waves return as echoes, and nonlinearly propagate through the tissue to produce harmonic components. The echo signal is sent as a reception signal to the Golay unit 17 through the preamplifier of the pulser/preamplifier unit 15 and a reception delay circuit 16. The reception delay circuit 16 performs beam forming at the time of reception and controls the direction and focusing of a beam. The reception delay circuit 16 may be formed from a plurality of circuit sets for forming a plurality of beams and perform concurrent reception. After beam forming, A/D conversion is performed. The reception signal is sampled with a sampling frequency suitable for signal processing and converted into a digital signal.

Transmission/reception of ultrasound waves by the pulser/preamplifier unit 15 and processing by the Golay unit 17 are performed in accordance with a phase-coded pulse compression scheme using a Golay code.

The Golay code is constituted by a pair of complementary code series (a code train of "1" and "−1"). The code "1" indicates phase modulation of 0° (no phase modulation) and the code "−1" indicates phase modulation of $\pi$. Ultrasound transmission/reception is repeated at least twice (two rates) in each direction (each ultrasound scanning line).

At the first rate, the phase of a reference waveform signal(carrier wave signal) is discretely modulated in accordance with one of the two types of code series. The transducer elements are driven in accordance with the phase-modulated waveform signal (first code signal). As a consequence, ultrasound waves are generated, and the resultant echo set is received, thereby generating a reception signal (first reception signal) with directivity.

At the second rate, the phase of a reference waveform signal is discretely modulated in accordance with the other of the two types of code series. The transducer elements are driven in accordance with the phase-modulated waveform signal (second code signal). As a consequence, ultrasound waves are generated, and the resultant echo set is received, thereby generating a reception signal (second reception signal) with directivity.

A Golay processor 24 of the Golay unit 17 convolutes the first and second code signals in the first and second reception signals, respectively, and adds the resultant signals, thereby generating a signal having a long depth reach and high distance resolution (Golay processing). A detecting circuit 25 detects this signal to generate image data. This image data is transformed into data in a rectangular coordinate system and interpolated by a displaying unit 18. The resultant data is then output in a video scheme to a monitor 13.

During the time difference between the first and second rates, the motion of the tissue in the object causes a phase difference corresponding to the motion of the tissue between the first and second reception signals. As described in "Description of the Related Art", this causes range sidelobes.

In this case, the motion of the tissue between the first and second rates is detected as the phase difference between the first and second reception signals. A typical method using a Doppler technique will be described as an example. Transmission/reception is repeated at two rates in the same direction, and the complex number of the signal obtained at one rate at each depth is multiplied by the complex number of the signal obtained at the other rate at the corresponding depth. A phase argument is then obtained from the multiplication result. In the autocorrelation method, similar processing is performed between a plurality of rates to obtain a complex vector product. This case can be regarded as a special case to which the autocorrelation method is applied, in which the number of data is two. When the obtained phase argument is normalized with $2\pi$, and the product of the normalized value and the wavelength of a barycentric frequency representing the fundamental wave is calculated, the displacement of the tissue between the two rates can be obtained. The actual displacement in the living body corresponds to ½ the displacement obtained in this case.

As described above, there are many techniques of detecting the phase difference between two reception signals at each depth. However, these techniques are based on the premise that two reception signals originate from the same transmission waveform signal. As described above, the first and second code signals are phase-modulated in accordance with the first and second code series of the Golay code. Without any processing, therefore, a change in scattering distribution such as motion cannot be separated from a change in transmission waveform, and hence a phase difference caused by the motion of the tissue between rates cannot be obtained.

Figure 4:
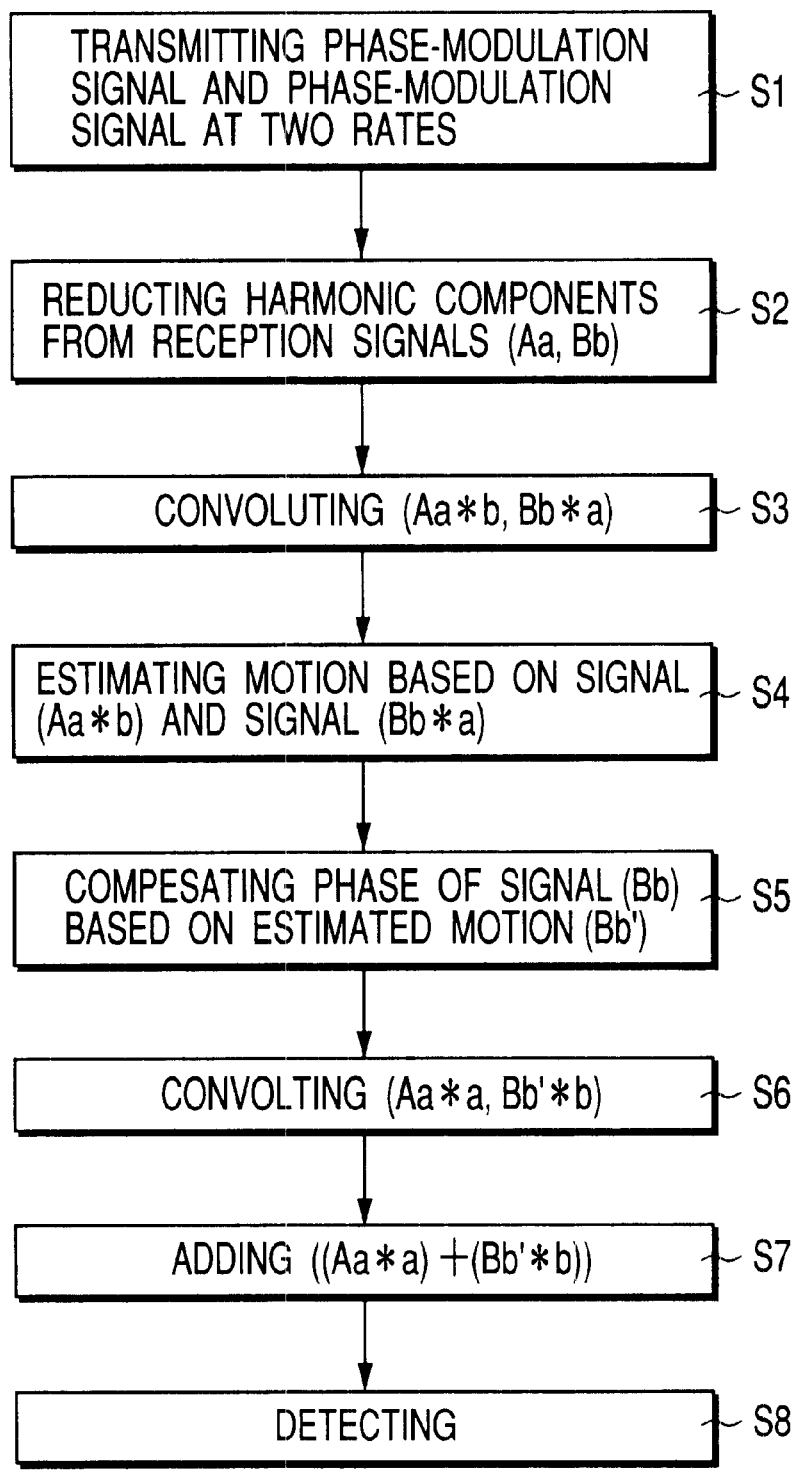
FIG. 4 is a flow chart showing a procedure in this embodiment.
Figure 5A:
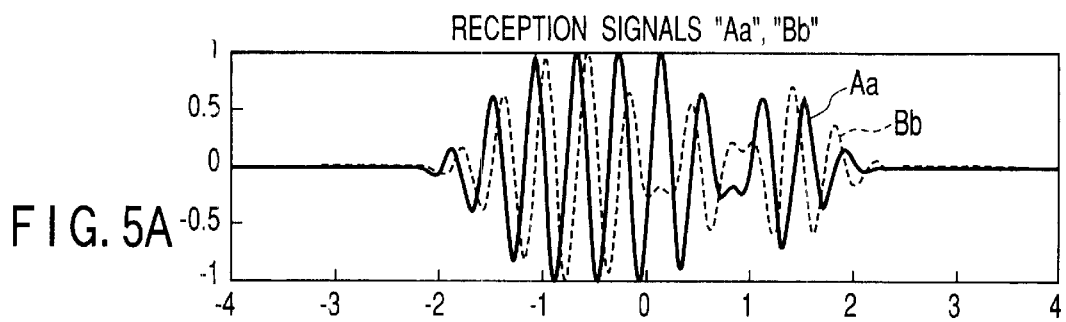
FIGS. 5A to 5I are graphs showing examples of signal waveforms corresponding to the procedure in FIG. 4.
Figure 5B:
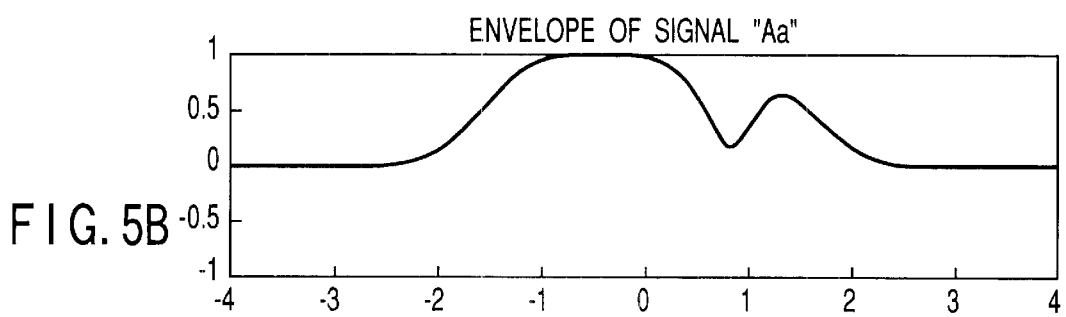
Figure 5C:
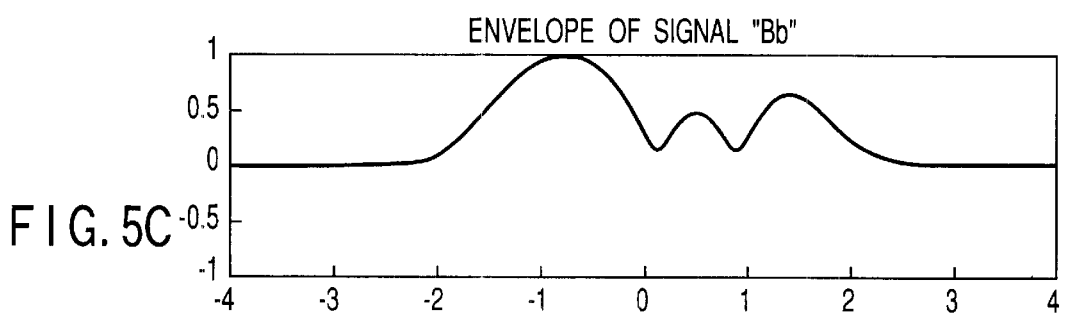

In this embodiment, this problem is solved by a motion estimating processor 21. First of all, as shown in FIG. 4, in order to improve the motion estimation precision, i.e., the precision of phase difference detection, unstable harmonic components in the first and second reception signals acquired in step S1 are reduced by a harmonic component reducing filter 20 to emphasize the fundamental wave component (S2). FIG. 5A shows an example of the waveform of a first reception signal "Aa" corresponding to a first code signal "a" of the first code series with the first rate, and an example of the waveform of a second reception signal Bb corresponding to a second code signal b of the second code series with the second rate. These first and second reception signals are separately subjected to orthogonal detection (I/Q) in the reception delay circuit 16. Therefore the carrier frequencies are removed from the signals, and the signals are shifted into a base band. With this operation, a real part and imaginary part are obtained. For the sake of descriptive convenience, these waveforms will be described as absolute value waveforms. FIG. 5B shows the envelope of the first reception signal "Aa". FIG. 5C shows the envelope of the second reception signal "Bb".

Figure 5D:
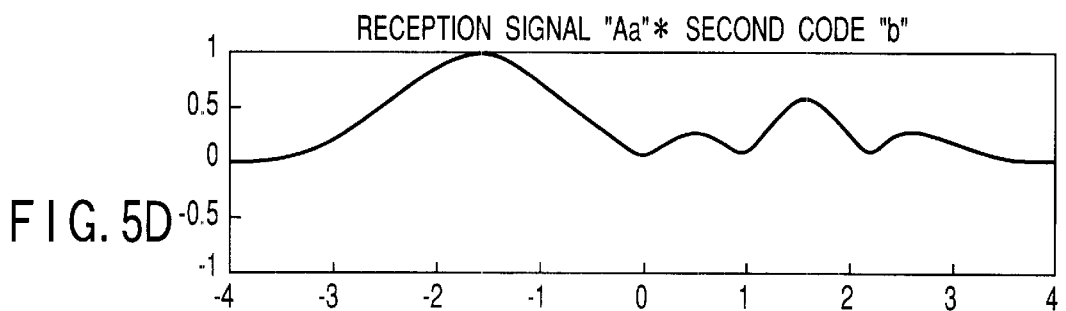
Figure 5E:
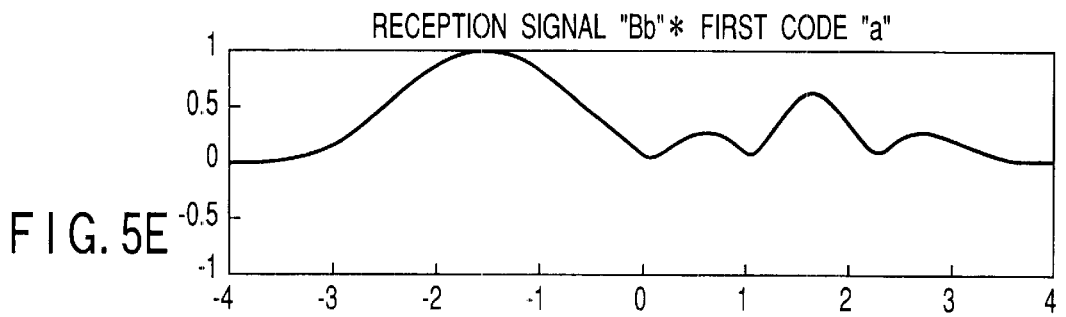

The motion estimating processor 21 convolutes the waveform signals of the opposite code "b" and "a" in the first and second reception signals "Aa" and "Bb" whose harmonic components are reduced, respectively. More specifically, the second code "b" used at the second rate is convoluted in the first reception signal "Aa" acquired with the first code series "a" at the first rate (FIG. 5D), whereas the first code signal "a" used at the first rate is convoluted in the second reception signal "Bb" acquired with the second code series "b" at second rate (FIG. 5E).

A signal "Aab" generated by the convolution of the second code "b" and the first reception signal "Aa" is given by convolution signal "Aab"=first reception signal "Aa"*second code "b"

In addition, since the first reception signal "Aa" is expressed by the convolution of the first code(waveform signal by the first code) "a" and a scattering distribution "A" at the first rate, the above expression can be rewritten as convolution signal "Aab"=first reception signal "Aa"*second code "b"=scattering distribution "A"*first code "a"* second code "b"

A signal "Bba" generated by the convolution of the first code "a" and the second reception signal "Bb" is given by convolution signal "Bba"=reception signal "Bb"*first code "a"

In addition, since the second reception signal "Bb" is expressed by the convolution of the second code (waveform signal by the second code) "b" and a scattering distribution "B" at the second rate, the above expression can be rewritten as convolution signal "Bba"=reception signal "Bb"*first code "a"= scattering distribution "B"*second code "b"*first code "a"

Figure 5F:
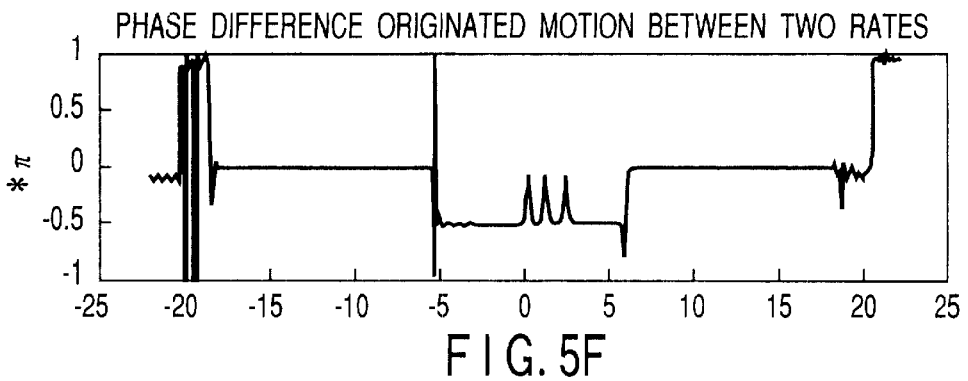

The scattering distribution "A" at first rate is substantially equal to the scattering distribution "B" at second rate. Therefore the convolution signals "Aab" and "Bba" are basically the same except for a phase difference originating from only the motion of the tissue. The motion estimating processor 21 obtains the phase difference between the reception signals Aab and Bba at each depth. This makes it possible to estimate the motion of the tissue between the two rates (S4). FIG. 5F shows a change in phase difference in the depth direction.

A motion compensating processor 23 then processes the first reception signal "Aa" at the first rate and the second reception signal "Bb" at the second rate to eliminate the phase difference obtained by the motion estimating processor 21. The first and second reception signals "Aa" and "Bb" bypass the filter 20, are directly supplied from the reception delay circuit 16 to the motion compensating processor 23. Therefore, the first and second reception signals "Aa" and "Bb" containing harmonic components are processed by the motion compensating processor 23, together with the fundamental wave component.

Figure 5G:
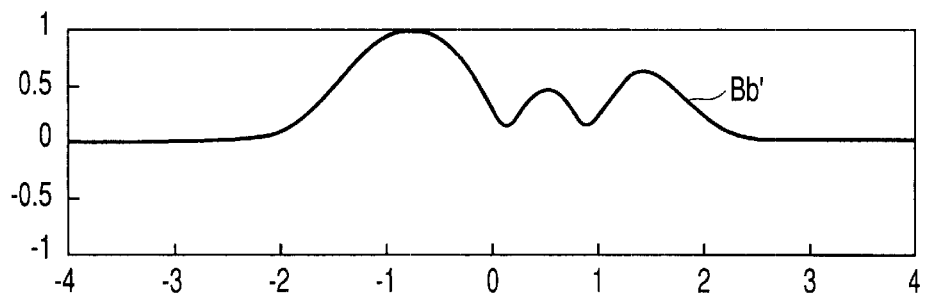

More specifically, the motion compensating processor 23 modulates the phase of the second reception signal "Bb" at the second rate at each depth on the basis of the phase difference obtained by the motion estimating processor 21 (S5). FIG. 5G shows a phase compensated reception signal "Bb'" with the second rate. The motion compensating processor 23 may modulate the phase of the second reception signal "Bb" at the first rate at each depth on the basis of the phase difference obtained by the motion estimating processor 21. Alternatively, the motion compensating processor 23 may modulate the phases of the first and second reception signals "Aa" and "Bb" at each depth on the basis of the phase difference obtained by the motion estimating processor 21.

Figure 5H:
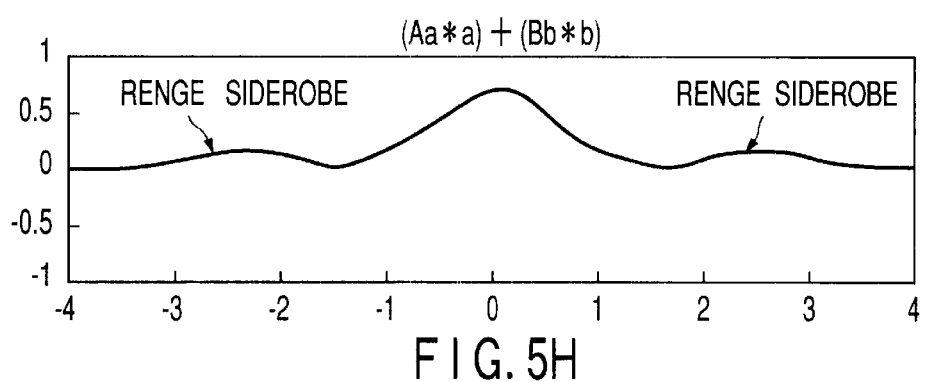
Figure 5I:
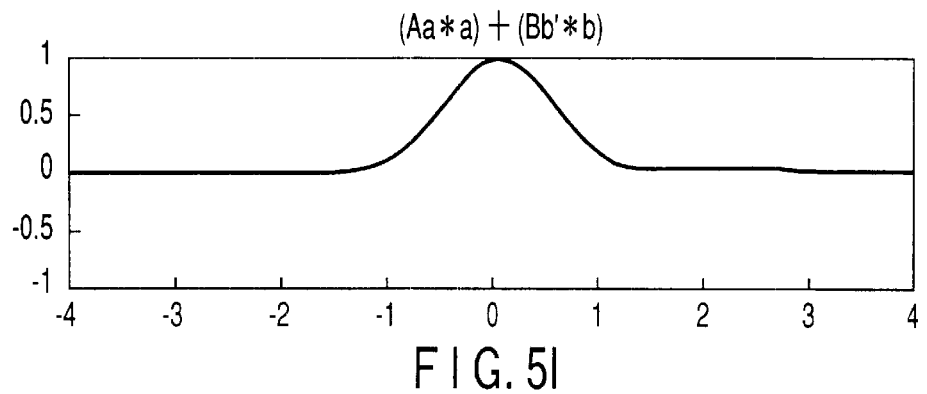

The Golay processor 24 convolutes the first code signal "a" in the first reception signal "Aa". The Golay processor 24 also convolutes the second code signal "b" in the motion-compensated second reception signal. "Bb'" (S6). In addition, the Golay processor 24 adds the two convolution signals (Aaa) and (Bb'b) (S7). This generates a reception signal (third reception signal) having a long depth reach and high distance resolution with reduced range sidelobes caused by the motion of the tissue between the rates. FIG. 5I shows the waveform of this third reception signal. FIG. 5H shows the waveform of a reception signal without motion compensation as a comparative example. As compared with the reception signal in FIG. 5H, the range sidelobe in the third reception signal is reduced, and its main component is enhanced.

Figure 6:
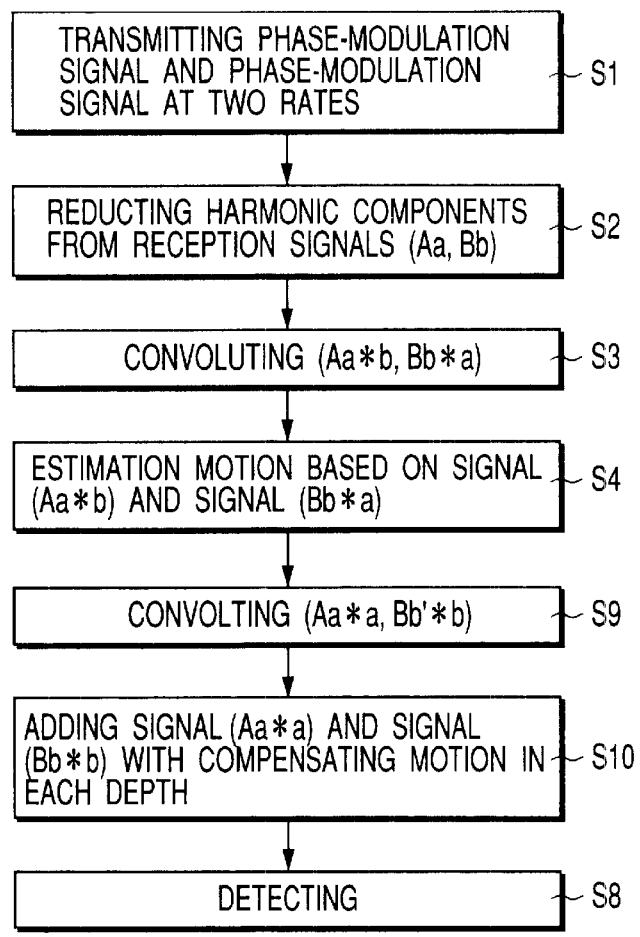
FIG. 6 is a flow chart showing another procedure in this embodiment.

In the above description, phase compensation is performed before the convolution in step S6. As shown in FIG. 6, however, the first and second reception signals A and B may be added while the timing of addition is shifted in accordance with the phase difference at each depth in addition processing in step S10.

Figure 7:
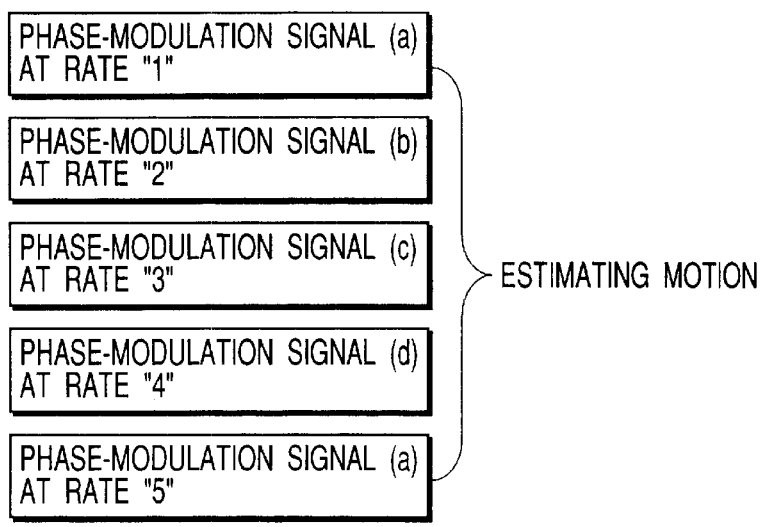
FIG. 7 is a view showing a modification of this embodiment.

Consider a case wherein ultrasound waves that are phase-modulated in accordance with a code series set are transmitted at three or more rates. FIG. 7 shows a case wherein ultrasound waves are transmitted at five rates by using four types of waveform signals that are phase-modulated in accordance with four types of code series. In such a case, the phase difference caused by the motion of the tissue between rates can be detected and phase compensation can be done on the basis of the detected phase difference by using a method simpler than the above method. Obviously, this method can be applied to the above method. Referring to FIG. 7, an ultrasound wave that is phase-modulated in accordance with one of the four types of code series, preferably a phase-modulation signal with the same code series as the first rate, is transmitted as a wave with the fifth rate, i.e., the last rate. With this operation, the transmission waveform with first rate 1 becomes identical to that with the last rate. By obtaining the phase difference between the reception signal with first rate 1 and the reception signal with last rate 5, therefore, the motion of the tissue between first rate 1 and last rate 5 can be estimated. The phase difference caused by the motion of the tissue between two consecutive rates can be estimated by dividing the phase difference between the reception signal with first rate 1 and the reception signal with last rate 5 by the number of rates −1, i.e., 4 (=5−1) in FIG. 7. Phase compensation may be done in the same manner as described above on the basis of the estimated phase difference.

As a method of estimating the motion of the tissue by using the convolution signals Aab and Bba, a method of obtaining a cross-correlation function at each depth is available in addition to the method of obtaining phase differences. A signal deviation at each depth can be known by detecting a time difference having the peak value of a cross-correlation function.

The motion compensating processor 23 shifts one of the reception signals at each depth so as to eliminate the time difference on the basis of the time difference obtained by the motion estimating processor 21. Alternatively, the motion compensating processor 23 calculates a phase difference corresponding to the time difference from the fundamental frequency, and performs modulation at each depth.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object;
   a first processor configured to convolute the second code in the first reception signal, convolute the first code in the second reception signal, and detect a phase difference between the two signals, the phase difference representing a motion of a tissue of the object between the first and second rates;
   a second processor configured to compensate at least one of the first and second reception signals on the basis of the phase difference;
   a third processor configured to convolute the first and second codes in the compensated first and second reception signals, respectively, add the two signals, and generate a third reception signal; and
   a unit configured to generate image data on the basis of the third reception signal.

2. An apparatus according to claim 1, wherein the first and second codes constitute Golay codes.

3. An apparatus according to claim 1, further comprising a filter which reduces harmonic components in the first and second reception signals and enhances a fundamental wave component.

4. An apparatus according to claim 3, wherein said first processor detects the phase difference between the first and second reception signals processed by said filter.

5. An apparatus according to claim 4, wherein said second processor compensates the first and second reception signals which are not processed by said filter.

6. An apparatus according to claim 1, wherein said second processor modulates a phase of at least one of the first and second reception signals on the basis of the phase difference.

7. An ultrasonic diagnostic apparatus comprising:

a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object;

a first processor configured to convolute the second code in the first reception signal, convolute the first code in the second reception signal, and detect a phase difference between the two signals, the phase difference representing a motion of a tissue of the object between the first and second rates;

a second processor configured to convolute the first and second codes in the first and second reception signals, respectively, add the two signals upon giving a time shift corresponding to the phase difference, and generate a third reception signal; and a unit configured to generate image data on the basis of the third reception signal.

8. An apparatus according to claim 7, wherein the first and second codes constitute Golay codes.

9. An apparatus according to claim 7, further comprising a filter which reduces harmonic components in the first and second reception signals and enhances a fundamental wave component.

10. An apparatus according to claim 9, wherein said first processor detects the phase difference between the first and second reception signals processed by said filter.

11. An apparatus according to claim 10, wherein said first processor compensates the first and second reception signals which are not processed by said filter.

12. An ultrasonic diagnostic apparatus comprising:

a transmitting/receiving unit configured to transmit an ultrasound wave to an object to be examined at a first rate in accordance with a first code, receive a first reception signal from the object, transmit an ultrasound wave to the object at a second rate in accordance with a second code complementary to the first code, and receive a second reception signal from the object;

a first processor configured to convolute the second code in the first reception signal, convolute the first code in the second reception signal, and detect a cross-correlation function between the two signals, the cross-correlation function representing a motion of a tissue of the object between the first and second rates;

a second processor configured to compensate at least one of the first and second reception signals on the basis of the cross-correlation function;

a third processor configured to convolute the first and second codes in the compensated first and second reception signals, respectively, add the two signals, and generate a third reception signal; and a unit configured to generate image data on the basis of the third reception signal.

13. An apparatus according to claim 12, wherein the first and second codes constitute Golay codes.

14. An apparatus according to claim 12, further comprising a filter which reduces harmonic components in the first and second reception signals and enhances a fundamental wave component.

15. An apparatus according to claim 14, wherein said first processor detects the cross-correlation function between the first and second reception signals processed by said filter.

16. An apparatus according to claim 15, wherein said second processor compensates the first and second reception signals which are not processed by said filter.

17. An ultrasonic diagnostic apparatus comprising:

a transmitting/receiving unit configured to transmit an ultrasound wave to an object to be examined in accordance with a first code at a first rate, receive a first reception signal, transmit an ultrasound wave to the object in accordance with a second code at a second rate, and receive a second reception signal from the object;

a first processor configured to estimate a motion of a tissue in the object between the first and second rates on the basis of the first and second reception signals and the first and second codes;

a second processor configured to compensate the first and second reception signals on the basis of the estimated motion; and a unit configured to generate image data on the basis of the compensated first and second reception signals.

18. An apparatus according to claim 17, wherein said first processor convolutes the second code in the first reception signal, convolutes the first code in the second reception signal, and estimates the motion of the tissue on the basis of the signals.

19. An apparatus according to claim 18, wherein said first processor obtains a phase difference between the signal obtained by convoluting the second code in the first reception signal and the signal obtained by convoluting the first code in the second reception signal as the motion of the tissue.

20. An ultrasonic diagnostic apparatus comprising:

a transmitting/receiving unit configured to transmit ultrasound waves modulated in accordance with codes at rates, receive reception signals;

a first processor configured to estimate a motion of a tissue in the object between a pair of the rates on the basis of reception signals of ultrasound waves corresponding to same code;

a second processor configured to compensate the reception signals on the basis of the estimated motion; and a unit configured to generate image data on the basis of the compensated reception signals.

* * * * *